(12) United States Patent
Suga et al.

(10) Patent No.: US 8,507,674 B2
(45) Date of Patent: Aug. 13, 2013

(54) QUORUM SENSING INHIBITOR

(75) Inventors: Hiroaki Suga, Tokyo (JP); Jun Igarashi, Tokushima (JP)

(73) Assignees: The University of Tokyo, Tokyo (JP); Otsuka Chemical Co., Ltd., Osaka-shi (JP)

(*) Notice: Subject to any disclaimer, the term of this patent is extended or adjusted under 35 U.S.C. 154(b) by 386 days.

(21) Appl. No.: 12/739,554

(22) PCT Filed: Nov. 12, 2008

(86) PCT No.: PCT/JP2008/070583
§ 371 (c)(1),
(2), (4) Date: Apr. 23, 2010

(87) PCT Pub. No.: WO2009/063901
PCT Pub. Date: May 22, 2009

(65) Prior Publication Data
US 2010/0256369 A1 Oct. 7, 2010

(30) Foreign Application Priority Data

Nov. 13, 2007 (JP) ................................. 2007-294817

(51) Int. Cl.
*C07D 239/70* (2006.01)
(52) U.S. Cl.
USPC ........................................................ 544/282
(58) Field of Classification Search
USPC ........................................................ 544/282
See application file for complete search history.

(56) References Cited

U.S. PATENT DOCUMENTS

| | | | |
|---|---|---|---|
| 4,022,897 A * | 5/1977 | Yale et al. | 514/259.4 |
| 4,219,649 A | 8/1980 | Knoll | |
| 4,259,344 A | 3/1981 | Gonczi | |
| 4,291,036 A * | 9/1981 | Knoll et al. | 514/259.4 |
| 5,753,664 A * | 5/1998 | Aono et al. | 514/259.4 |
| 7,498,292 B2 | 3/2009 | Suga | |
| 2008/0027115 A1 | 1/2008 | Suga | |

FOREIGN PATENT DOCUMENTS

| | | |
|---|---|---|
| GB | 1 408 433 | 10/1975 |
| JP | 48-36193 | 5/1973 |
| JP | 54-48795 | 4/1979 |
| JP | 2006-508929 A1 | 3/2006 |
| JP | 2006-512290 A1 | 4/2006 |
| WO | WO 02/18342 A2 | 3/2002 |

OTHER PUBLICATIONS

La Motta, et al., Pyrido[1,2-a]pyrimidin-4-one Derivatives as a Novel Class of Selective Aldose Reductase Inhibitors Exhibiting Antioxidant Activity, J. Med. Chem., 50, 4917-4927 (2007).*
F. Fülöp, I. et al., "Nitrogen Bridgehead Compounds. IX. Synthesis and Reactions of 2,3-Disubsituted Pyrido[1,2-α]pyrimidin-4-ones (1)", Journal of Heterocyclic Chemistry, vol. 16, No. 3, pp. 457-460.
Harry L. Yale, "9-Hydroxy-2-methyl-4H-pyrido[1,2-α]pyrimidin-4-one, 9-Hydroxy-2-phenyl-4H-pyrido[1,2-α] pyrimidin-4-one, 9-Methyl-2-phenyl-4H-pyrido[1,2-α]-pyrimidin-4-one, Ethyl 9-Hydroxy-4H-pyrido[1, 2-α]pyrimidin-4-one-3-carboxylate and Their Derivatives", Journal of Heterocyclic Chemistry, vol. 12, No. 2, pp. 427-431.
Supplementary European Search Report dated Mar. 5, 2012, in counterpart European Application No. EP 08849623.
Z. Meszaros, et al.; "4-Oxo-4H-pyrido[1,2-a]pyrimidines;" Chemical Abstracts; vol. 85; No. 15; Oct. 11, 1976; p. 465 and cover sheet, Abstract No. 108662m (2 Sheets.).
P.L. Ferrarini, et al.; "Synthesis of some 4H-Pyrido[1,2-a]Pyrimidin-4-ones investigated as antimicrobial agents;" IL Farmaco; vol. 50; No. 1; 1995; pp. 69-72 (4 Sheets.).
J. Kim, et al; "Quorum sensing and the LysR-type transcriptional activator ToxR regulate toxoflavin biosynthesis and transport in Burkholderia glumae;" Molecular Microbiology; vol. 54; No. 4; 2004; pp. 921-934 (14 Sheets.)/p. 2.
International Search Report for International Application No. PCT/JP2008/070583 dated Dec. 3, 2008.

* cited by examiner

Primary Examiner — Erich A Leeser
(74) Attorney, Agent, or Firm — Kratz, Quintos & Hanson, LLP (57) ABSTRACT

The present invention provides a control agent that is extremely effective in controlling bacterial diseases. The quorum sensing inhibitor and bacterial disease control agent for agricultural and horticultural use of the present invention contain a pyrimidinone compound represented by General Formula (1):

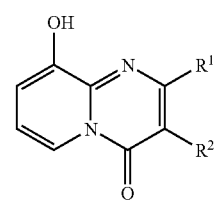

(1)

wherein $R^1$ represents a $C_{1-5}$ alkyl group or a phenyl group, and $R^2$ represents a hydrogen atom or a $C_{1-5}$ alkyl group, provided that $R^1$ cannot be a methyl group when $R^2$ represents a hydrogen atom.

9 Claims, 3 Drawing Sheets

QUORUM SENSING INHIBITOR

TECHNICAL FIELD

The present invention relates to a quorum sensing inhibitor.

BACKGROUND ART

Some types of bacteria have a gene network (a quorum sensing function) that detects its own bacteria count and controls its pathogenic expression. It is known that various types of bacteria, such as opportunistic infection bacteria, use quorum sensing and collectively act to express the pathogenicity of substances such as toxins after obtaining the number of bacteria necessary to resist the defense mechanism of a host or hostile organism.

Bacterial plant diseases are known to be intractable. Most common, commercially available agents that are effective for treating plant diseases caused by mold (filamentous fungi) are not effective for treating bacterial diseases; therefore, only a limited number of agents, such as inorganic or organic copper fungicides, streptomycin, oxolinic acids, and biotic pesticides, are currently used as bacterial disease control agents. Furthermore, even when these control agents are used, a satisfactory control effect cannot always be achieved depending on the type of farm product. In recent years, the generation of oxolinic-acid-resistant *Burkholderia glumae* and the like has been reported. This makes the control of bacterial plant diseases even more difficult. *Burkholderia glumae*, which is an organism that causes bacterial plant disease, is known to use quorum sensing to discharge a burst of toxin after infecting rice, to thereby cause disease (Non-Patent Document 1).

Patent Document 1 discloses that a specific type of pyrimidinone compound can be used as a central nervous system stimulant. However, Patent Document 1: nowhere discloses the control effect of the pyrimidinone compound on bacterial plant diseases. In fact, as is clear from Test Example 1 described later, the pyrimidinone compound specifically disclosed in Patent Document 1 has absolutely no control effect on bacterial diseases.

Patent Document 2 discloses that a specific type of pyrimidinone compound has an analgesic action. However, it is silent about the control effect of the pyrimidinone compound on bacterial plant diseases.

Patent Document 3 discloses that a specific type of amide compound acts on bacteria to inhibit biofilm (biomembrane) formation. However, the document is silent about the control effect of the amide compound on bacterial plant diseases. In fact, as is clear from the Test Example described later, the amide compound of Patent Document 3 has no control effect on bacterial diseases.

Under the current situation where there is an insufficient variety of agents that are effective for controlling bacterial plant diseases, there is a strong demand for the development of an agent that effectively controls bacterial plant diseases.

Patent Document 1: Japanese Unexamined Patent Publication No. 1973-36193

Patent Document Japanese Unexamined Patent Publication No. 1979-48795

Patent Document Japanese Unexamined: Patent Publication No. 2006-512290

Non-Patent Document 1: Molecular Microbiology, (2004)

DISCLOSURE OF THE INVENTION

Problem to be Solved by the Invention

An object of the present invention is to provide a control agent that is extremely effective on bacterial diseases.

Means for Solving the Problem

The present inventors have conducted extensive research to achieve the above object. As a result, they found that a specific pyrimidinone compound has an inhibiting effect on the quorum sensing of specific bacteria. In particular, the present inventors found that a pyrimidinone compound suppresses the toxin production of bacteria, inhibits the deposit of biofilms, and strips off and removes deposited biofilms, to achieve the above object. The present invention has been accomplished based on these findings.

The present invention provides a quorum sensing inhibitor comprising a pyrimidinone compound represented by General Formula (1):

(1)

wherein $R^1$ is a $C_{1-5}$ alkyl group or a phenyl group, $R^2$ is a hydrogen atom or a $C_{1-5}$ alkyl group; provided that $R^1$ cannot be a methyl group when $R^2$ is a hydrogen atom.

The present invention provides a bacterial disease control agent for agricultural and horticultural use comprising the pyrimidinone compound represented by General Formula (1).

The present invention provides a biofilm formation inhibitor comprising the pyrimidinone compound represented by General Formula (1).

The present invention provides a biofilm remover comprising the pyrimidinone compound represented by General Formula (1).

Examples of $C_{1-5}$ alkyl groups in General Formula (1) include methyl, ethyl, n-propyl, isopropyl, n-butyl, isobutyl, sec-butyl, tert-butyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl and like straight chain or branched chain $C_{1-5}$ alkyl groups.

It is preferable that the pyrimidinone compound represented by General Formula (1), which is the active ingredient of the present invention, be a pyrimidinone compound wherein $R^1$ is a straight chain or branched chain $C_{2-5}$ alkyl group, and $R^2$ is a hydrogen atom. A pyrimidinone compound represented by General Formula (1), wherein $R^1$ is a straight chain $C_{3-5}$ alkyl group and $R^2$ is a hydrogen atom, is particularly preferable.

It is preferable that the pyrimidinone compound represented by General Formula (1), which is the active ingredient of the present invention, be a pyrimidinone compound wherein $R^1$ is a straight chain or branched chain $C_{1-3}$ alkyl group, and $R^2$ is a straight chain or branched chain $C_{1-5}$ alkyl group. A pyrimidinone compound wherein $R^1$ is a straight chain $C_{1-3}$ alkyl group, and $R^2$ is a methyl group is more preferable.

The pyrimidinone compound represented by General Formula (1), which is the active ingredient of the present invention, can be prepared by, for example, allowing Compound (2) and Compound (3) to react in an aromatic hydrocarbon solvent (e.g., benzene, toluene, xylene) under reflux according to the process shown in Reaction Formula 1. More specifically, the pyrimidinone compound can be prepared according to the Production Examples described later.

Reaction Formula 1 wherein $R^1$ and $R^2$ are the same as those described above, and $R^3$ is a $C_{1-5}$ alkyl group.

The pyrimidinone compound of the present invention is effective for controlling diseases caused by bacteria that belong to the *Erwinia* species, *Burkholderia* species or *Xanthomonas* species, such as *Xanthomonas oryzae* pv. *oryzae*, *Burkholderia glumae*, *Burkholderia plantarii*, *Burkholderia syringae*, *Xanthomonas campestris* pv. *citri*, *Erwinia amylovora*, *Xanthomonas campestris* pv. *pruni*, *Burkholderia syringae* pv. *morsprunorum*, *Xanthomonas campestris*, *Burkholderia syringae* pv. *maculicola*, *Erwinia carotovora*, *Burkholderia cicihorii*, *P. marginars*, *P. viridiflava*, *Erwinia carotovora* subsp. *cartovora*, and *Burkholderia solanacearum*, etc.). It is extremely effective for controlling *Burkholderia*, in particular, *Burkholderia glumae*.

The pyrimidinone compound of the present invention inhibits the toxin production of *Burkholderia glumae* (see Test Example 9 described later). *Burkholderia glumae* uses quorum sensing to regulate the production of a so-called ahpF (alkyl hydroperoxide reductase subunit F) enzyme, which is involved in the aerotolerance mechanism of bacteria. Accordingly, the pyrimidine compound of the present invention inhibits the expression of ahpF and thereby causes *Burkholderia glumae* to self-destruct due to air oxidation.

When the pyrimidinone compound represented by General Formula (1) is used as a bacterial disease control agent for agricultural and horticultural use, the pyrimidinone compound may be used as the control agent without any additives. However, the pyrimidinone compound may also be used after being mixed with various carriers in a solid, liquid, gaseous or like form. If necessary, surfactants, binders, dispersants, stabilizers and like preparation adjuvants, etc., may be added to the pyrimidinone compound so as to form emulsions, wettable powders, dry-flowable preparations, flowable preparations, water soluble preparations, granules), fine granules, parvules, powders, liniments, sprays, aerosols, microcapsules, fumigants, smoke fungicides, etc.

The content of the pyrimidinone compound represented by General Formula (1), which is the active ingredient of these preparations, can be suitably selected from a broad range depending on various conditions, including their formulation, application site, etc. Generally, the content of the pyrimidinone compound is about 0.01 to 95 wt. %, and preferably about 0.1 to 50 wt. % per total weight of the preparation.

Examples of solid carriers that may be mixed in the preparation of the present invention include kaolin clay, diatomaceous earth, bentonite, Fubasami clay, acid clay and like clays; talc, ceramics, cerite, quartz, sulfur, activated carbon, silica carbonate, silica hydrate and like inorganic minerals; chemical fertilizer and like fine powders; granular materials; etc.

Examples of liquid carriers that may be mixed in the preparation of the present invention include water; alcohol; acetone, methyl ethyl ketone and like ketones; n-hexane, cyclohexane, kerosene, light oil and like aliphatic or cycloaliphatic hydrocarbons; benzene, toluene, xylene, naphthalene and like aromatic hydrocarbons; ethyl acetate, butyl acetate and like esters; acetonitrile, isobutyronitrile and like nitriles; diisopropyl ether, dioxane and like ethers; N,N-dimethylformamide, N,N-dimethylacetamide and like acid amides; dichloromethane, trichloroethane, carbon tetrachloride and like halogenated hydrocarbons; dimethyl sulfoxide; soybean oil, cotton seed oil and like vegetable oils.

Examples of gaseous carriers that may be mixed in the preparation of the present invention include those generally used as propellants, such as butane gas, liquefied petroleum gas, dimethyl ether, and carbon dioxide gas.

Examples of surfactants that may be mixed in the preparation of the present invention include polyoxyethylene alkyl ether, polyoxyethylene alkyl ester, polyethylene sorbitan alkyl ester and like nonionic surfactants; alkylbenzene sulfonate, alkyl sulfosuccinate, alkyl sulfate, polyoxyethylene alkyl sulfate, allyl sulfonate, lignin sulfate and like anionic surfactants; etc.

Examples of binders and dispersants include casein, gelatin, polysaccharide (starch, gum arabic, cellulose derivatives, alginic acid, etc.), lignin derivatives, bentonite, saccharides, synthetic water-soluble polymers (polyvinyl alcohol, polyvinyl pyrrolidone, polyacrylic acids, etc.), etc.

Examples of stabilizers include PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oil, mineral oil, surfactant, fatty acid or an ester thereof, etc.

The preparation of the present invention may be colored using an organic or inorganic dye.

The preparation of the present invention may be used as it is or may be diluted with water or a like solvent. In the case of a granule, powder and the like, the preparation of the present invention is generally used without diluting. When an emulsion, wettable powder, flowable preparation and the like is diluted using water or a like solvent, the concentration of the active ingredient is generally about 0.0001 to 100 wt. %, and preferably about 0.001 to 10 wt. %.

The bacterial disease control agent for agricultural and horticultural use of the present invention may be pre-mixed with other agents such as a herbicide, insecticide, nematicide, miticide, bactericide, plant growth regulator, synergist, soil conditioner, etc. Furthermore, the preparation of the present invention may be used in combination with the above-mentioned agents.

Examples of methods for applying the bacterial disease control agent for agricultural and horticultural use of the present invention to cultivated plants include ground liquid spraying, ground solid spraying, aerial liquid spraying, aerial solid spraying, foliar spraying, use in a facility, soil incorporation, application during soil watering, surface treatment (seed coating, application treatment, etc.), seed box application, single flower treatment, root treatment, etc. Conventionally, seed treatment (disinfection) is often conducted to prevent bacterial plant diseases. The bacterial disease control agent for agricultural and horticultural use of the present invention is also effective by conducting foliar application even after a bacterial disease is found. This allows various application methods to be employed.

The amount of the pyrimidinone compound used in the bacterial disease control agent for agricultural and horticultural use of the present invention is not particularly limited and can be selected from a wide range depending on various conditions, including the form of the preparation, the application method, the application season, the application site, the type of farm products to which it is applied, the type of the targeted bacteria, and the like. The amount of the pyrimidinone compound used is generally about 0.1 to 1,000 g and preferably about 10 to 500 g per 100 $m^2$. When an emulsion, wettable powder, flowable preparation or the like is diluted with water, the concentration is generally about 1 to 1,000 ppm, and preferably about 10 to 500 ppm. Granules, powders, etc., are usually used as they are without diluting.

The quorum sensing inhibitor of the present invention can control not only bacterial diseases on agricultural and horticultural plants but also *Burkholderia aeruginosa, Porphyromonas gingivalis, Tannerella forsythensis, Actinobacillus actinomycetemcomitans, Prevotella intermedia, Eikenella corrodens, Campyrobacter rectus, Fusobacterium necleatum, Treponema denticola, Actinomyces naeslundii, Streptococcus mutans, Burkholderia mallei, Burkholderia pseudomallei*, etc.

*Burkholderia aeruginosa* and *Porphyromonas gingivalis* are known to use quorum sensing to form a biofilm (which is also referred to as a "biomembrane"). A biofilm is a mucous film formed by the secretion of microorganisms. Several kinds of microorganisms exist in the biofilm to form a complex (a colony) that adheres to the surface of a solid. To be more specific, a biofilm is an aggregation of microorganisms surrounded by slime that is secreted or discharged therefrom. The pyrimidine compound of the present invention prevents *Burkholderia aeruginosa* or *Porphyromonas gingivalis* from forming a biofilm (i.e., exhibits a biofilm formation inhibition effect) or strips off and removes an already formed biofilm (i.e., exhibits a biofilm removal effect). Similar to *Burkholderia glumae, Burkholderia mallei* and *Burkholderia pseudomallei* do not form a distinct biofilm; however, they regulate toxin production by quorum sensing. The pyrimidine compound of the present invention inhibits the quorum sensing of *Burkholderia mallei* and *Burkholderia pseudomallei*.

Because the distinguishing effects of the pyrimidine compound of the present invention, i.e., inhibiting the formation of a biofilm and also stripping off and removing an already formed biofilm, the pyrimidine compound of the present invention can be used in a wide range of applications. Among these applications, the pyrimidine compound of the present invention can be effectively used to treat intractable biofilm infectious diseases; therefore, it is expected to contribute significantly to the fundamental treatment of such diseases.

For example, *Burkholderia aeruginosa* is constantly present in the natural environment, and proliferates to form a biofilm when even small amounts of an organic substance and moisture exist. Therefore, *Burkholderia aeruginosa* causes hospital infections, microbial substitutions, opportunistic infections, etc., and deteriorates the hygienic conditions of water and other pipes, water tanks, etc. Furthermore, plaque formed by *Porphyromonas gingivalis* takes the form of a biofilm, and causes intraoral diseases such as dental caries, periodontosis, periodontoclasia; foul breath; etc. It is conventionally known that removing plaque is an important way to enhance oral hygiene and treat intraoral diseases. However, biofilms work like a defensive membrane against bactericide and like agents; therefore, the effect of the agents is hardly exhibited.

The use of the quorum sensing inhibitor of the present invention inhibits the formation of biofilm by *Burkholderia aeruginosa* and facilitates the removal of an already formed biofilm to enhance the hygienic conditions in hospitals; pipes in households, factories, etc.; water tanks; etc. The quorum sensing inhibitor of the present invention can thereby be used to effectively prevent or treat hospital infections and other problems. Furthermore, the quorum sensing inhibitor of the present invention inhibits the formation of biofilms by *Porphyromonas gingivalis* on teeth, gingiva, intraoral dental materials, etc., and facilitates the removal of the biofilms already formed on the surfaces thereof. The quorum sensing inhibitor of the present invention can thereby be used to effectively prevent or treat caries and like dental diseases; periodontitis, periodontoclasia and like periodontal diseases; stomatitis and like intraoral diseases; etc.

As shown in the Test Example described later, the pyrimidinone compound represented by General Formula (1) exhibits a biofilm removal action and a biofilm formation inhibition action. Accordingly, the pyrimidinone compound represented by General Formula (1) is useful as an active ingredient of a composition (a biofilm remover or a biofilm formation inhibitor) that is used to strip off and remove a biofilm or to inhibit the formation of a biofilm.

The pyrimidinone compound represented by General Formula (1) is effective against bacteria that form a biofilm and against an already formed biofilm. In particular, the pyrimidinone compound exhibits an excellent biofilm removal effect and biofilm formulation inhibition activity against *Burkholderia aeruginosa, Porphyromonas gingivalis*, and biofilms formed thereby.

Accordingly, the present invention provides a biofilm remover or a biofilm formation inhibitor (hereunder, the biofilm remover and the biofilm formation inhibitor may be collectively called a "preparation") comprising the pyrimidinone compound represented by General Formula (1) as an active ingredient.

The present preparation may consist of the pyrimidinone compound represented by General Formula (1) or may be a composition that is formed into a preparation suitable for application by a known method in combination with arbitrary carriers and additives. There is no limitation to the form of the present preparation, and examples thereof include tablets, powders, granules, pills, powder syrups, capsules (hard capsules and soft capsules) and like solid preparations; creams, ointments, gels and like paste- or gel-like preparations; solutions, suspensions, milky lotions, syrups, elixirs, sprays, aerosols and like liquid preparations; etc.

There is no limitation to the content of the pyrimidinone compound represented by General Formula (1) in the present preparation as long as it can exhibit the biofilm removal effect or the biofilm formation inhibition effect. The content of the pyrimidinone compound can be selected from the range of generally 0.001 to 99 wt. %, preferably 0.01 to 50 wt. %, and more preferably 0.05 to 10 wt. % per total 100 wt. % of the preparation.

As long as the present preparation contains the pyrimidinone compound represented by General Formula (1) in an amount such that the biofilm removal effect or the biofilm formation inhibition effect can be achieved, the present preparation may contain other components within a range that does not adversely affect the effect of the present invention. These components may be selected depending on the application purpose and object of the biofilm remover or the biofilm formation inhibitor. Although not limited to these, examples of other components include excipients, binders, dispersants, thickeners, lubricants, pH adjusters, solubilizing agents and like carriers generally used for the production of preparations; and antibiotics, antimicrobial agents, bactericides, antiseptic agents, builders, bleaching agents, enzymes, chelating agents, antifoaming agents, coloring agents (dyes, pigments, etc.), softening agents, humectants, surfactants, antioxidants, fragrances, corrigents, odor-masking agents, solvents, etc.

It is preferable that the present preparation contain, in addition to the pyrimidinone compound represented by General Formula (1), for example, a tetracycline bactericide such as minocycline hydrochloride; a cationic bactericide such as triclosan, cetylpyridinium chloride, or benzethonium chloride; or an antibacterial agent or bactericide such as a macrolide antibiotic.

The present preparation may additionally contain a compound that improves antibacterial or bactericide activity. Examples of such a compound include basic amino acids such as arginine, lysine, and histidine; various enzymes including starch modification enzymes such as farnesol, transglucosidase, and CGTase; and starch hydrolases such as α-amylase.

The preparation of the present invention is widely applicable to places where a biofilm has been formed and places that suffer from the detrimental effects of such biofilm formation.

The preparation of the present invention can be used, for example, in the following manner to remove biofilms deposited in industrial areas, circulating-type bathtubs, etc. The preparation of the present invention, having been processed into a suspension liquid, wettable powder, or water-soluble powder, is circulated in the pipes of the target equipment, or sprayed on the target portion of the equipment. The preparation of the present invention can also take the form of a high-concentration liquid, or a solid preparation such as a tablet, powder, or grain agent supplied to a water tank so that the preparation is diluted or dissolved in the water and applied to the target portion. When the preparation of the present invention is used as a medicinal preparation, it can take a form that is suitable for oral administration, parenteral administration, or local administration. When the preparation of the present invention is processed into an oral administered preparation, it can take the form of a mouthwash.

The appropriate usage amount of the preparation of the present invention varies depending on the target object and dosage form. It differs particularly for sustained-release formulations, and therefore cannot be clearly defined. However, when used to prevent or treat a biofilm infection, for example, an appropriate per-day dosage amount of the preparation of the present invention is generally 1 ng/mL to 100 mg/mL, and preferably 10 ng/mL to 10 mg/mL based on the dosage of the compound or salt thereof of the present invention (e.g., the gross quantity for humans is 300 mg).

The present invention provides an oral composition containing the biofilm remover, or the biofilm formation inhibitor. The present invention was made based on the fact that the biofilm remover or the biofilm formation inhibitor of the present invention containing pyrimidinone compound (1) or salt thereof as an active ingredient has a particularly remarkable effect of removing/stripping off a biofilm formed by interoral bacteria or of inhibiting the biofilm formation ability possessed by interoral bacteria.

Examples of oral compositions to which the present invention is applicable include dentifrices such as toothpaste, a powder dentifrice, a liquid dentifrice, a moisturized dentifrice; mouthwashes and oral cleansers in the form of a troche, tablet, liquid, gum, gummy candy, film, etc.; gingival medicines in the form of a cream, ointment or gel; a troche; chewing gum; gargles in the form of a liquid, powder or tablet; and cleaning agents for artificial teeth or dental materials in the form of a tablet or foaming agent.

The amount of biofilm remover or biofilm formation inhibitor added to the oral composition is such that the content (the total amount) of the pyrimidinone compound represented by General Formula (1), which is the active ingredient of the biofilm remover or biofilm formation inhibitor, is generally 0.001 to 99 wt. % or more, preferably 0.01 to 50 wt. %, and more preferably 0.05 to 10 wt. % per 100 wt. % of the composition.

In addition to the above-mentioned components, the oral composition of the present invention may further contain the following components within the generally used amount depending on its type and form.

Abrasive

Examples of abrasives include silica abrasives such as silica gel, precipitable silica, igneous silica, hydrous silicic acid, anhydrous silicic acid, titanium silicate, zeolite, aluminosilicate and zirconosilicate; calcium primary phosphate, calcium secondary phosphate dihydrate, calcium secondary phosphate non-hydrates, calcium pyrophosphate, magnesium tertiary phosphate, calcium tertiary phosphate, aluminum hydroxide, alumina, calcium carbonate light, calcium carbonate heavy, magnesium carbonate, magnesium tertiary phosphate, zirconium silicate, insoluble sodium metaphosphate, insoluble calcium metaphosphate, titanium oxide, synthetic resin abrasive; etc. These abrasives may be used singly or in combination. When these abrasives are used (e.g., in dentifrices, etc.), the amount of the abrasive is not limited, but generally 3 to 80 wt. % and preferably 10 to 50 wt. % per 100 wt. % of the oral composition.

Humectant or Viscous Agent

Examples of humectants and viscous agents include polyhydric alcohols such as glycerin, concentrated glycerin, diglycerin, ethylene glycol, dipropylene glycol, polyethylene glycol, propylene glycol, polypropylene glycol, and 1,3-butyleneglycol; and sugar-alcohols such as xylitol, maltitol, and lactol. These humectants and viscous agents may be used singly or in combination.

Binder

Examples of binders include alginates and derivatives thereof such as alginic acid, sodium alginate, propylene glycol alginate, calcium-containing sodium alginate, potassium alginate, calcium alginate, and ammonium alginate; gums such as carrageenan (Iota, Lambda, and Kappa), xanthan gum, tragacanth gum, karaya gum, gum arabic, locust bean gum, and guar gum; celluloses such as carboxymethylcellulose sodium, methylcellulose, ethylcellulose, cellulose acetate, and hydroxyethylcellulose sodium; gelatin, agar, polyvinyl alcohol, sodium polyacrylate, carboxyvinyl polymer, polyvinyl pyrrolidone, carbopol, silica gel, aluminum silica gel, and thickening nature silica. These binders may be used singly or in combination. When such binders are used (e.g., in dentifrices, etc.), the amount is not particularly limited, but preferably 0.1 to 10 wt. % per 100 wt. % of the oral composition.

Foaming Agents

Examples of foaming agents include sodium lauryl sulfate, lauroylsarcosine sodium, alkyl sulfo monosodium succinate, palm-oil-fatty-acid mono-glycerol sulfone sodium, α-olefin sulfone sodium, N-acylamino acid salts such as N-acyl-glutamate, 2-alkyl-N-carboxymethyl-N-hydroxyethyl imidazolinium betaine, maltitol ester of fatty acid, sucrose ester of fatty acid, polyglyceryl ester of fatty acid, fatty acid diethanolamide, polyoxyethylenesorbitan monostearate, polyoxyethylene hydrogenated castor oil, and polyoxyethylene ester of fatty acid. These foaming agents may be used singly or in combination.

Surfactants

Anion surfactants, cation surfactants, nonionic surfactants, and amphoteric surfactants are all usable.

Examples of anion surfactants include sodium lauryl sulfate, sodium myristyl sulfate, sodium N-lauroylsarcosinate, sodium N-myristoylsarcosinate, sodium dodecylbenzenesulfonate, hydrogenated coconut fatty acid monoglyceride mono-sodium sulfate, sodium lauryl sulfosulfate, sodium α-olefin sulfonate, N-acylglutamates such as N-palmitoyl sodium glutamate, and N-acyltaurates such as sodium N-methyl-N-acyltaurinate. Examples of nonionic surfactants include sucrose esters of fatty acid such as sucrose ester of fatty acid and maltose ester of fatty acid; sugar-alcohol esters of fatty acid such as maltitol ester of fatty acid and lactol ester of fatty acid; alkylol amide; polyoxyethylene sorbitan esters of fatty acid such as polyoxyethylenesorbitan monostearate; polyoxyethylene esters of fatty acid such as polyoxyethylene hydrogenated castor oil; fatty acid diethanolamides such as lauryl acid mono- or di-ethanolamide, sorbitan ester of fatty acid, polyoxyethylene higher alcohol ether, polyoxyethylene polyoxypropylene copolymer, polyoxyethylene polyoxypropylene ester of fatty acid, polyglyceryl ester of fatty acid, and Pluronic. Examples of amphoteric surfactants include 2-alkyl-N-carboxymethyl-N-hydroxyethyl imidazolium betaine; N-alkyldiaminoethyl glycine such as N-lauryl diaminoethyl glycine and N-myristyl diaminoethyl glycine; and sodium N-alkyl-1-hydroxyethylimidazolin betainate. These surfactants may be used singly or in combination.

Sweetening Agents

Examples of sweetening agents include saccharin sodium, aspartame, stevioside, stevia extract, paramethoxy cinnamic aldehyde, neohesperidyl dihydrochalcone, perillartine, glycyrrhizine, and thaumatin. These sweetening agents may be used singly or in combination.

Antiseptic Agents

Examples of antiseptic agents include parabens, such as methylparaben, ethylparaben, propylparaben, and butylparaben; sodium benzoate, phenoxyethanol, and alkyldiaminoethylglycine hydrochloride. These antiseptics may be used singly or in combination.

Perfume Components

Examples of perfume components include l-menthol, anethole, menthone, cineole, limonene, carvone, methyl salicylate, ethyl butyrate, eugenol, thymol, n-decylalcohol, citronellol, α-terpineol, citronellyl acetate, linalool, ethyl linalool, vanillin, thymol, peppermint, cinnamic aldehyde, and trans-2-hexenal. These perfume components may be used singly or in combination. Note that these components may be used as pure (purified) products, or may be added in the form of crude products containing these components, such as essential oils (e.g., lemon oil, orange oil, sage oil, rosemary oil, cassia and cinnamon oil, pimento oil, cinnamon leaf oil, beefsteak plant oil, wintergreen oil, clove oil, and eucalyptus oil).

In addition to the foregoing perfume components, other components or essential oils, such as aliphatic alcohol or esters thereof, terpene carbon hydride, phenolether, aldehyde, ketone, and lactone, may be used insofar as the effects of the present invention are not impaired. The amount of these perfume components is preferably 0.02 to 2 wt. %, per 100 wt. % of the total oral composition.

Antibacterial Components

Examples of antibacterial components include antibacterial metals, such as silver, copper, zinc, and metal salts thereof with low water solubility (e.g., silver oxide, silver chloride, silver carbonate, silver phosphate, copper hydroxide, copper gluconate, zinc oxide, zinc citrate, zinc stearate, zinc undecylenate, zinc hydroxide, zinc oxalate, and zinc phosphate), copper chlorophyll, cetylpyridium chloride, benzalkonium chloride, triclosan, hinoki thiol, and lysozyme chloride.

Antiseptic Component

Examples of antiseptic components include nonionic antimicrobial agents such as parabens, sodium benzoate and triclosan; and cationic antimicrobial agents such as benzethonium chloride and cetylpyridinium chloride.

Active Ingredients for Use in the Oral Cavity

Examples of active ingredients for use in the oral cavity include lysozyme chloride, sodium fluoride, potassium fluoride, sodium monofluorophosphate, polyethyleneglycol, polyvinyl pyrrolidone, hinoki thiol, ascorbic acid, ascorbic acid salts, chlorhexidine salts, cetylpyridinium chloride, benzalkonium chloride, benzethonium chloride, bisabolol, triclosan, isopropylmethylphenol, tocopherol acetate, ε-aminocaproic acid, tranexamic acid, aluminum hydroxyl allantoin, aluminum lactate, dihydrocholesterol, glycyrrhetinic acid, glycyrrhizic acid salts, copper chlorophyllin salts, sodium chloride, guaiazulene sulfonic acid salts, dextranase, pyridoxine hydrochloride, tranexamic acid, sodium chloride, Vitamins C and E, various enzymes (e.g., dextranase, amylase, protease, mutanase, and pectinase), tartar control agents such as azulene and polyphosphate; nicotine removers such as polyethylene glycol and polyvinyl pyrrolidone; and hyperesthesia prophylactic agents such as aluminum lactate and potassium nitrate. These oral active ingredients may be used singly or in combination.

Other Additives

Examples of other additives include colorants and pigments such as Food Blue No. 1 and titanium oxide; antioxidants such as dibutylhydroxytoluene; and corrigents such as tea leaf dry distilled solution and sodium glutamate.

The oral composition of the present invention can be manufactured by any common procedure, and there is no limitation to the production method thereof. The resulting oral composition in the form of, for example, toothpaste, is packed into an aluminum tube, laminated tube, glass evaporation tube, plastic tube, plastic bottle, aerosol container or the like during the production or selling process, and removed from the packing container when used.

The oral composition of the present invention prevents the formation of biofilms by intraoral bacteria and removes already formed intraoral biofilms, thereby effectively preventing the generation of bacterial flora. Further, by using the oral composition of the present invention together with an antimicrobial agent, the antibacterial effects of the present invention can be enhanced, thereby providing an oral composition having an excellent plaque formation inhibition effect and an antibacterial effect. Accordingly, the oral composition of the present invention is effective for preventing or treating intraoral diseases such as caries (dental caries), periodontosis and periodontal diseases (e.g., periodontoclasia, etc.). The oral composition of the present invention is also effectively usable for preventing or refreshing foul breath caused by caries (dental caries), periodontitis or periodontal disease (e.g., periodontoclasia).

Effect of the Invention

The pyrimidinone compound represented by General Formula (1) exhibits an excellent control effect against intractable bacterial plant diseases. The pyrimidinone compound represented by General Formula (1) is remarkably effective for controlling the toxin production of, in particular, Burkholderia glumae and the like. Accordingly, the pyrimidinone compound represented by General Formula (1) is suitably usable as a bacterial disease control agent for agricultural and horticultural use.

The pyrimidinone compound represented by General Formula (1) is effective for controlling the quorum sensing of Burkholderia aeruginosa, Porphyromonas gingivalis, etc., and is suitably used as a biofilm formation inhibitor or a biofilm remover.

EXPLANATION OF REFERENCE NUMERALS

Figure 4:
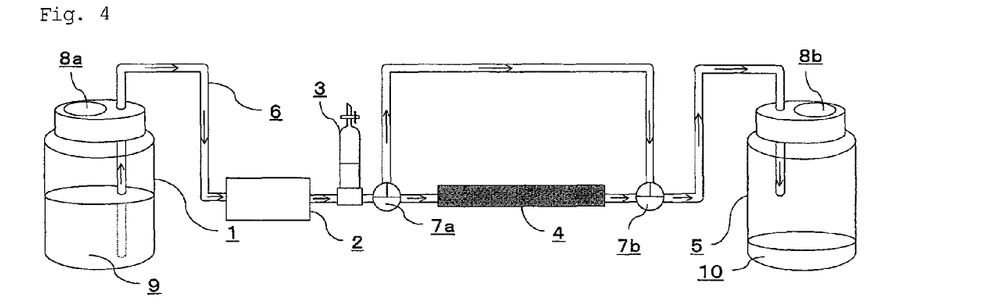
FIG. 4 is a schematic diagram showing the flow cell system used in Test Example 7 and Test Example 8.

1: Culture medium bottle (produced by Nunc)
2: Pump (4-channel peristaltic pump ISM935: produced by ISMATEC)
3: Air removal section (employing a glass column with cock)
4: Glass cell (Observation Glass Capillary FC91 (1 mm×1 mm×14 mm): produced by BioSurface Technology)
5: Waste fluid tank (produced by Nunc)
6: Silicon tube (diameter: 1.5 mm)
7a, 7b: Three-way turncock (produced by Termo)
8a, 8b: Membrane filter (0.44 μm: produced by Millipore)
9: Culture medium
10: Waste fluid

EXAMPLES

The present invention is explained in detail below with reference to Production Examples and Test Examples of the pyrimidinone compound represented by General Formula (1). However, the scope of the present invention is not limited to these examples.

Production Example 1

Production of 2-n-propyl-9-hydroxy-4H-pyrid[1,2-a]pyrimidin-4-one (hereunder, this compound is referred to as "Compound (1)")

3-Hydroxy-2-aminopyridine (3.13 g, 28.5 mmol) and ethyl 3-oxohexanoate (4.50 g, 28.5 mmol) were dissolved in xylene (15 mL). The resulting solution was stirred at room temperature for about 12 hours, and then heated and allowed to react under reflux for about 16 hours. The reaction mixture was cooled and then concentrated under reduced pressure. The resulting residue was subjected to extraction using ethyl acetate. The thus-obtained organic layer was washed with an aqueous saturated sodium chloride solution, dried over magnesium sulfate, and then concentrated under reduced pressure. The resulting residue was purified using silica gel chromatography (developing solvent: n-hexane/ethyl acetate=9/1), obtaining Compound (1).

Quantity Yield: 3.8 g (18.5 mmol)
Percent Yield: 65%
$^1$H-NMR (CDCl$_3$, 500 MHz): 1.01 ppm (t, 3H), 1.76 ppm (m, 2H), 2.66 ppm (m, 2H), 6.32 ppm (s, 1H), 7.02 ppm (m, 1H), 7.14 ppm (m, 1H), 7.26 ppm (s, 1H), 8.53 ppm (m, 1H).

Production Example 2

Production of 9-hydroxy-2-n-pentyl-4H-pyrid[1,2-a]pyrimidin-4-one (hereunder, this compound is referred to as "Compound (2)")

Compound (2) was obtained in the same manner as Production Example 1 except that ethyl 3-oxooctanoate was used instead of ethyl 3-oxohexanoate.

Quantity Yield: 3.0 g (13.1 mmol)
Percent Yield: 46%
$^1$H-NMR (CDCl$_3$, 500 MHz): 0.92 ppm (t, 3H), 1.37 ppm (m, 4H), 1.74 ppm (m, 2H), 2.67 ppm (m, 2H), 6.32 ppm (s, 1H), 7.03 ppm (m, 1H), 7.13 ppm (m, 1H), 7.26 ppm (s, 1H), 8.52 ppm (m, 1H).

Production Example 3

Production of 3-ethyl-9-hydroxy-2-methyl-4H-pyrid[1,2-a]pyrimidin-4-one (hereunder, this compound is referred to as "Compound (3)")

Compound (3) was obtained in the same manner as Production Example 1 except that ethyl 2-acetylbutanoate was used instead of ethyl 3-oxohexanoate.

Quantity Yield: 3.7 g (18.0 mmol)
Percent Yield: 63%
$^1$H-NMR (CDCl$_3$, 500 MHz): 1.22 ppm (t, 3H), 2.55 ppm (s, 3H), 2.77 ppm (m, 2H), 7.02 ppm (m, 1H), 7.10 ppm (m, 1H), 7.31 ppm (s, 1H), 8.51 ppm (m, 1H).

Production Example 4

Production of 3-n-butyl-9-hydroxy-2-methyl-4H-pyrid[1,2-a]pyrimidin-4-one (hereunder, this compound is referred to as "Compound (4)")

Compound (4) was obtained in the same manner as Production Example 1 except that ethyl 2-acetylhexanoate was used instead of ethyl 3-oxohexanoate.

Quantity Yield: 4.4 g (18.8 mmol)
Percent Yield: 66%
$^1$H-NMR (CDCl$_3$, 500 MHz): 0.98 ppm (t, 3H), 1.45 ppm (m, 2H), 1.56 ppm (m, 2H), 2.52 ppm (s, 3H), 2.72 ppm (m, 2H), 6.99 ppm (m, 1H), 7.06 ppm (m, 1H), 7.28 ppm (s, 1H), 8.48 ppm (m, 1H).

Production Example 5

Production of 9-hydroxy-2-isopropyl-4H-pyrid[1,2-a]pyrimidin-4-one (hereunder, this compound is referred to as "Compound (5)")

Compound (5) was obtained in the same manner as Production Example 1 except that ethyl 3-oxo-4-methyl-pentanoate was used instead of ethyl 3-oxohexanoate.

Quantity Yield: 1.9 g (9.1 mmol)
Percent Yield: 32%
$^1$H-NMR (CDCl$_3$, 500 MHz): 1.30 ppm (m, 6H), 2.97 ppm (m, 1H), 6.18 ppm (s, 1H), 7.02 ppm (m, 1H), 7.13 ppm (m, 1H), 7.34 ppm (s, 1H), 8.50 ppm (m, 1H).

Production Example 6

Production of 9-hydroxy-2-tert-butyl-4H-pyrid[1,2-a]pyrimidin-4-one (hereunder, this compound is referred to as "Compound (6)")

Compound (6) was obtained in the same manner as Production Example 1 except that ethyl 3-oxo-4,4-dimethyl-pentanoate was used instead of ethyl 3-oxohexanoate.

Quantity Yield: 4.7 g (21.7 mmol)
Percent Yield: 76%
$^1$H-NMR (CDCl$_3$, 500 MHz): 1.39 ppm (m, 9H), 6.53 ppm (s, 1H), 7.02 ppm (m, 1H), 7.16 ppm (m, 1H), 7.49 ppm (s, 1H), 8.52 ppm (m, 1H).

Production Example 7

Production of 9-hydroxy-2-phenyl-4H-pyrid[1,2-a]pyrimidin-4-one (hereunder, this compound is referred to as "Compound (7)")

Compound (7) was obtained in the same manner as Production Example 1 except that ethyl 3-oxo-3-phenyl-propanoate was used instead of ethyl 3-oxohexanoate.

Quantity Yield: 547 mg (2.3 mmol)
Percent Yield: 8%
$^1$H-NMR (CDCl$_3$, 500 MHz): 7.00 ppm (s, 1H), 7.10 ppm (m, 1H), 7.21 ppm (m, 1H), 7.52 ppm (m, 3H), 8.08 ppm (m, 2H), 8.58 ppm (m, 1H).

Production Example 8

Production of 9-hydroxy-2-ethyl-4H-pyrid[1,2-a]pyrimidin-4-one (hereunder, this compound is referred to as "Compound (8)")

Compound (8) was obtained in the same manner as Production Example 1 except that ethyl 3-oxo-pentanoate was used instead of ethyl 3-oxohexanoate.

Quantity Yield: 2.6 g (13.7 mmol)
Percent Yield: 48%
$^1$H-NMR (CDCl$_3$, 500 MHz): 1.33 ppm (t, 3H), 2.61 ppm (m, 2H), 6.28 ppm (s, 1H), 6.85 ppm (m, 1H), 7.04 ppm (m, 1H), 8.52 ppm (m, 1H).

Production Example 9

Production of 9-hydroxy-2-n-butyl-4H-pyrid[1,2-a]pyrimidin-4-one (hereunder, this compound is referred to as "Compound (9)")

Compound (9) was obtained in the same manner as Production Example 1 except that ethyl 3-oxoheptanoate was used instead of ethyl 3-oxohexanoate.

Quantity Yield: 2.4 g (11.1 mmol)
Percent Yield: 39%
$^1$H-NMR (CDCl$_3$, 500 MHz): 0.96 ppm (t, 3H), 1.41 ppm (m, 2H), 1.73 ppm (m, 2H), 2.68 ppm (m, 2H), 6.32 ppm (s, 1H), 7.02 ppm (m, 1H), 7.15 ppm (m, 1H), 8.52 ppm (m, 1H).

Production Example 10

Production of 9-hydroxy-2-isobutyl-4H-pyrid[1,2-a]pyrimidin-4-one (hereunder, this compound is referred to as "Compound (10)")

Compound (10) was obtained in the same manner as Production Example 1 except that ethyl 5-methyl-3-oxohexanoate was used instead of ethyl 3-oxohexanoate.

Quantity Yield: 3.7 g (16.8 mmol)
Percent Yield: 59%
$^1$H-NMR (CDCl$_3$, 500 MHz): 0.97 ppm (m, 6H), 2.18 ppm (m, 1H), 2.54 ppm (m, 2H), 6.30 ppm (s, 1H), 7.04 ppm (m, 1H), 7.10 ppm (m, 1H), 8.53 ppm (m, 1H).

Production Example 11

Production of 2-sec-butyl-9-hydroxy-4H-pyrid[1,2-a]pyrimidin-4-one (hereunder, this compound is referred to as "Compound (11)")

Compound (11) was obtained in the same manner as Production Example 1 except that ethyl 4-methyl-3-oxohexanoate was used instead of ethyl 3-oxohexanoate.

Quantity Yield: 2.6 g (11.8 mmol)
Percent Yield: 41%
$^1$H-NMR (CDCl$_3$, 500 MHz): 0.89 ppm (t, 3H), 1.28 ppm (t, 3H), 1.62 ppm (m, 1H), 1.78 ppm (m, 1H), 2.67 ppm (m, 1H), 6.33 ppm (s, 1H), 7.03 ppm (m, 1H), 7.11 ppm (m, 1H), 8.52 ppm (m, 1H).

Production Example 12

Production of 9-hydroxy-2-(2-pentyl)-4H-pyrid[1,2-a]pyrimidin-4-one (hereunder, this compound is referred to as "Compound (12)")

Compound (12) was obtained in the same manner as Production Example 1 except that ethyl 4-methyl-3-oxoheptanoate was used instead of ethyl 3-oxohexanoate.

Quantity Yield: 1.9 g (8.0 mmol)
Percent Yield: 28%

$^1$H-NMR (CDCl$_3$, 500 MHz): 0.90 ppm (t, 3H), 1.29 ppm (m, 4H), 1.55 ppm (m, 1H), 1.73 ppm (m, 1H), 2.77 ppm (m, 1H), 6.32 ppm (s, 1H), 7.02 ppm (m, 1H), 7.09 ppm (m, 1H), 8.52 ppm (m, 1H).

Comparative Production Example 1

Production of 2-n-propyl-4H-pyrid[1,2-a]pyrimidin-4-one ((hereunder, this compound is referred to as "Comparative Compound (1)")

Comparative Compound (1) was obtained in the same manner as Production Example 1 except that 2-aminopyridine was used instead of 3-hydroxy-2-aminopyridine and polyphosphoric acid was used as the reaction solvent instead of xylene.

Quantity Yield: 1.3 g (6.8 mmol)
Percent Yield: 24%
$^1$H-NMR (CDCl$_3$, 500 MHz): 1.00 ppm (t, 3H), 1.80 ppm (m, 2H), 2.67 ppm (m, 2H), 6.36 ppm (s, 1H), 7.11 ppm (m, 1H), 7.61 ppm (m, 1H), 7.74 ppm (m, 1H), 9.05 ppm (m, 1H).

Comparative Production Example 2: 2-n-pentyl-4H-pyrid[1,2-a]pyrimidin-4-one (hereunder, this compound is referred to as "Comparative Compound (2)")

Comparative Compound (2) was obtained in the same manner as Production Example 1 except that 2-aminopyridine was used instead of 3-hydroxy-2-aminopyridine, ethyl 3-oxohexanoate was used instead of ethyl 3-oxohexanoate, and polyphosphoric acid was used as the reaction solvent instead of xylene.

Quantity Yield: 1.7 g (8.0 mmol)
Percent Yield: 28%
$^1$H-NMR (CDCl$_3$, 500 MHz): 0.89 ppm (t, 3H), 1.36 ppm (m, 4H), 1.74 ppm (m, 2H), 2.67 ppm (m, 2H), 6.37 ppm (s, 1H), 7.11 ppm (m, 1H), 7.60 ppm (m, 1H), 7.71 ppm (m, 1H), 9.02 ppm (m, 1H).

Comparative Production Example 3

Production of 9-methoxy-2-n-propyl-4H-pyrid[1,2-a]pyrimidin-4-one (hereunder, this compound is referred to as "Comparative Compound (3)")

Comparative Compound (3) was obtained in the same manner as Production Example 1 except that 3-methoxy-2-aminopyridine was used instead of 3-hydroxy-2-aminopyridine, and polyphosphoric acid was used as the reaction solvent instead of xylene.

Quantity Yield: 1.6 g (7.4 mmol)
Percent Yield: 26%
$^1$H-NMR (CDCl$_3$, 500 MHz): 1.00 ppm (m, 3H), 1.79 ppm (m, 2H), 2.74 ppm (m, 2H), 4.06 ppm (s, 1H), 6.39 ppm (s, 1H), 7.00 ppm (m, 2H), 8.69 ppm (m, 1H).

Test Example 1

*Burkholderia glumae* was inoculated into an LB culture medium (produced by BD) (Difco LB Broth: containing tryptone (10.0 g), yeast extract (5.0 g), and sodium chloride (10.0 g)), and cultured at 37° C. overnight. The thus-cultured broth was subjected to bacterial collection using a centrifuge, washed with an LB culture medium twice using a fresh LB culture medium each time. Each of an LB culture media containing a 0.4% dimethyl sulfoxide (DMSO) solution of 40 µM or 60 µM of Compound (1) and a 0.4% DMSO that did not contain Compound (1) for a comparative test was added to the thus-obtained bacteria, followed by shake culturing for 12 or 24 hours. Each of the broths was filtered by a membrane filter (0.22 µm). 0.5 mL of ethyl acetate was added to 0.5 mL of supernate from which bacteria were removed, and then the quorum sensing (QS) signal molecules were extracted using ethyl acetate. The thus-obtained ethyl acetate layer was concentrated under reduced pressure, and the residue was re-dissolved in 20 µL of methanol, producing a test liquid.

The test liquid (1 µL) was spotted on TLC to separate C6-HSL and C8-HSL, which are QS signal molecules, under the condition of developing solvent: methanol/water=70/30. After the development, a TLC plate was well dried and a culture solution containing QS signal molecule detection bacteria (*Chromobacterium violaceum* CV026 strain) that had been pre-cultured in an LB culture medium and agar was applied to the TLC plate, followed by the detection of C6-HSL and C8-HSL. *Chromobacterium violaceum* is known as a bacterium that produces purple pigment (violacein) using the QS; therefore, the CV026 strain can be used to detect QS signal molecules (Microbiology, (1997), 143, 3703-3711, (2004), 54(4), 921-934, (2007), 64(1), 165-179). After applying the detected bacteria to the TLC plate, the TLC plate was subjected to overnight cultivation at 28° C. and then detection using violacein. For quantitative determination, calibration curves showing the violacein production from C6-HSL and C8-HSL that had been chemically synthesized were obtained. From the calibration curves, the production amounts of the QS signal molecules of each compound were obtained. Table 1 shows the results.

TABLE 1

| Concentration of | C6-HSL (ng/ml) | | C8-HSL (µg/ml) | |
|---|---|---|---|---|
| Compound (µM) | 12 hours | 24 hours | 12 hours | 24 hours |
| 0 | 163 | 536 | 16 | 55 |
| 40 | 163 | 0 | 14 | 0 |
| 60 | 167 | 0 | 13 | 0 |

Test Example 2

*Burkholderia glumae* was inoculated into an LB culture medium, and cultured at 37° C. overnight. The thus-obtained culture solution was subjected to bacterial collection using a centrifuge, washed with an LB culture medium twice using a fresh LB culture medium each time. To the bacterial cell a fresh LB culture medium was added to prepare a culture suspension of about $3.0×10^5$ cfu/mL. Thereafter, each of Compound (1), Compound (2), Compound (3), Compound (4), Compound (5), Compound (8) and Compound (9) produced in Production Examples 1-5 were added to the culture suspension in such a manner that their final concentration became 100 μM, followed by shake culturing for 36 hours. The number of microorganisms in the culture solution 24 hours and 36 hours after the initiation of the culturing were obtained by the following procedure. Specifically, a portion of the culture solution was removed and diluted 1,000-fold, and then seeded to an LB culture medium agar plate. The number of colonies were counted to obtain the number of microorganisms.

Figure 1:
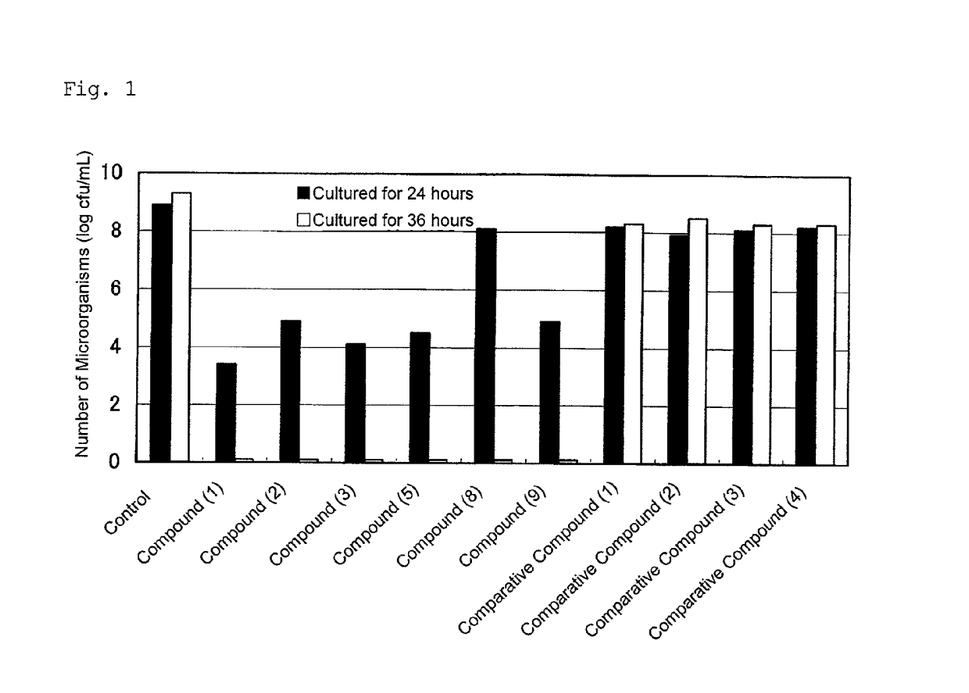
FIG. 1 is a graph showing the number of microorganisms that exist in the culture solution after being cultured for 24 hours and 36 hours in Test Example 2.

The same experiments were conducted, as comparative tests, using Comparative Compounds (1)-(3), which were produced in Reference Examples 1-3 and the below-explained compound (Comparative Compound (4)), which is disclosed in Patent Document 1, thereby obtaining the number of microorganisms. FIG. 1 shows the results.

Comparative Compound (4)

[Structure of Comparative Compound (4): a pyrido-pyrimidinone with OH and CH₃ substituents]

FIG. 1 indicates that the pyrimidinone compound of the present invention (Compounds (1) to (5), Compound (8) and Compound (9)) exhibit an excellent control activity against *Burkholderia glumae*, i.e., these compounds can kill almost all *Burkholderia glumae* after 36 hours of cultivation, and Comparative Compounds (1) to (4) exhibit little control activity against *Burkholderia glumae*.

Test Example 3

Figure 2:
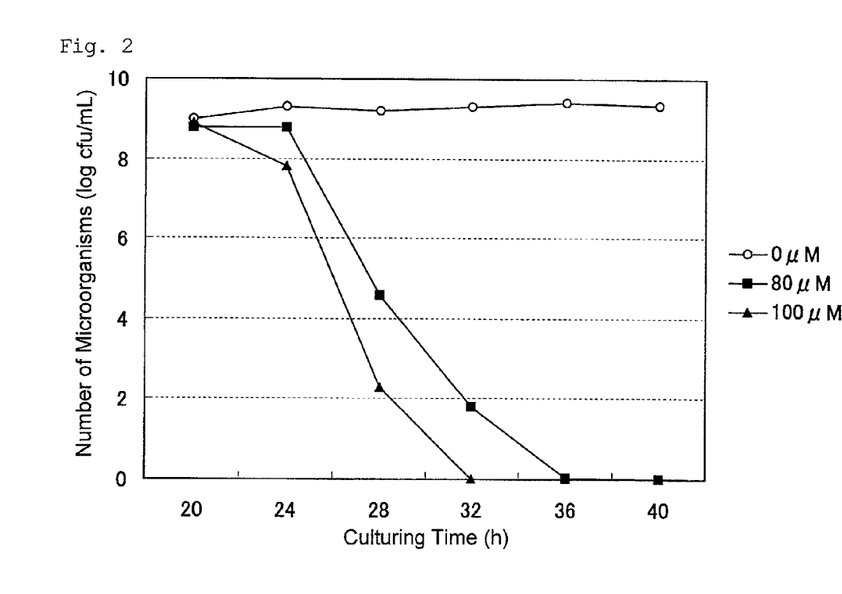
FIG. 2 is a graph showing the relationship between the culturing time and the number of microorganisms at each concentration of Compound (1) supplied in Test Example 3.

*Burkholderia glumae* was inoculated into an LB culture medium, and cultured at 37° C. overnight. The thus-obtained culture solution was subjected to bacterial collection using a centrifuge, washed with an LB culture medium twice using a fresh LB culture medium each time. To the bacterial cell a fresh LB culture medium was added to prepare a culture suspension of about $3.0×10^5$ cfu/mL. Thereafter, Compound (1) produced in Production Example 1 was added to the culture suspension in such a manner that its final concentration became a predetermined value (i.e., 0 μM, 80 μM, or 100 μM), followed by shake culturing for 40 hours. The number of microorganisms in the culture solution after a predetermined time (i.e., 20, 24, 28, 32, 36 and 40 hours) was obtained by the following procedure. Specifically, a portion of the culture solution was removed and diluted 1,000-fold, and then seeded to an LB culture medium agar plate. The number of colonies was counted to obtain the number of microorganisms. FIG. 2 shows the results.

FIG. 2 indicates that the pyrimidinone compound of the present invention (Compound (1)) exhibits an excellent control effect against *Burkholderia glumae*.

Test Example 4

*Burkholderia glumae* was inoculated into an LB culture medium, and cultured at 37° C. overnight. The thus-obtained culture solution was subjected to bacterial collection using a centrifuge, and washed with an LB culture medium twice using a fresh LB culture medium each time. To the bacterial cell a fresh LB culture medium was added, and then Compound (1) produced in Production Example 1 was added thereto in such a manner that its final concentration became a predetermined value (i.e., 0, 20, 40, 60, 80 or 100 μM), followed by shake culturing for 20 hours. The amount of toxoflavin produced by the bacterial cell in the culture solution was obtained by the following procedure.

Each culture solution was filtered by 0.22-μm membrane filter, and 1 mL of the filtrate was isolated. One mL of chloroform was added to the filtrate, followed by extraction. The thus-obtained chloroform layer was concentrated under reduced pressure, and an 80% (V/V) an aqueous methanol solution was added to and dissolved in the residue. The absorbance (at 260 nm) of the solution was measured, and the toxin doses were calculated from the calibration curve, which was obtained using a chemically synthesized standard toxin.

Figure 3:
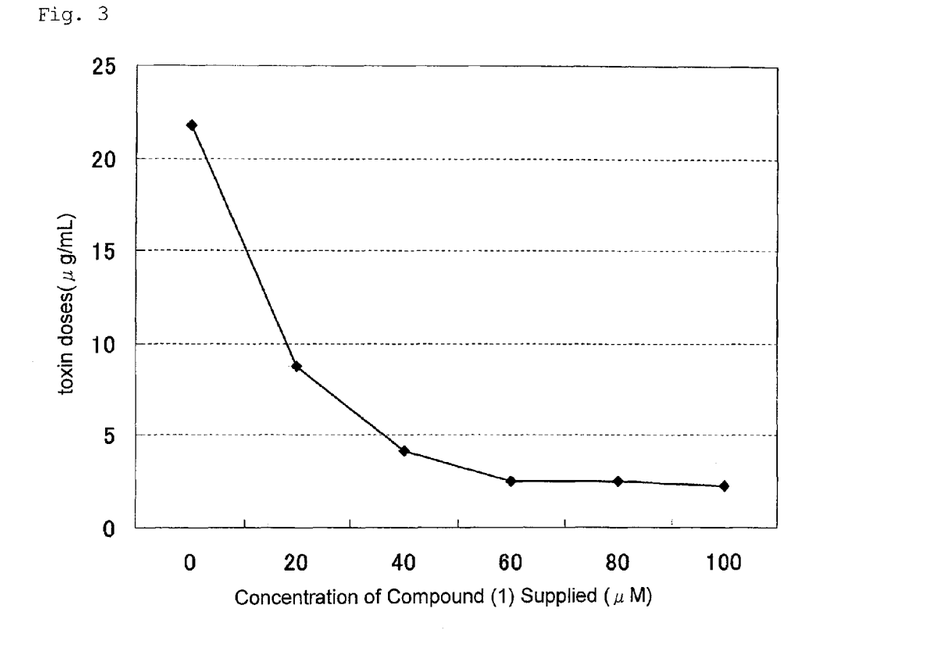
FIG. 3 is a graph showing the relationship between the concentrations (μM) of Compound (1) supplied and toxin doses (μg/mL) in Test Example 4.

FIG. 3 shows the results.

FIG. 3 indicates that when Compound (1) produced in Production Example 1 was added to *Burkholderia glumae*, the toxin doses produced by bacteria remarkably decreased by increasing the concentration of Compound (1).

Test Example 5

A dimethyl formamide solution (1,000 ppm) of Compound (1) was diluted with water to have a predetermined concentration (50, 100 or 200 μM) to prepare a test liquid. In a separate procedure, *Burkholderia glumae* were seeded to an LB culture medium and cultured overnight at 37° C., preparing a culture solution for infection.

Each test liquid (10 mL) was sprayed onto Korean rice (Milyang 23) raised in a hothouse until the flowering stage. The culture solution for infection was sprayed onto the rice one hour after the application of the test liquid. After cultivation for seven days, the onset of *Burkholderia glumae* infection on the rice was evaluated.

The evaluation was conducted by picking an ear from each plant, making a total of three ears. In each flower cluster (grain), the percentage of the portion that suffered from the onset of disease (i.e., the portion that turned brown) caused by the toxoflavin produced by *Burkholderia glumae* was visually observed and scored based on the scale shown below. The percentage of the total flower clusters was obtained and scored to indicate the onset of the disease.

Evaluation Criteria

The percentage that suffered from the onset of disease:
Less than 0.1%: 0
Not less than 0.1% and not greater than 20%: 1
Not less than 20% and not greater than 40%: 2
Not less than 40% and not greater than 60%: 3
Not less than 60% and not greater than 80%: 4
Not less than 80% to 100%: 5

In this evaluation, three flower clusters (grains) having the same conditions were prepared, and reproducibility was confirmed by repeating the same evaluation three times. The same evaluation was also conducted as a comparative test except that water was used instead of the test liquid. Further, the same evaluation was conducted to serve as a blank except that water was used instead of both the test liquid and the culture solution for infection.

Table 2 shows the results.

TABLE 2

| Score | Blank | Compound (1) | | | Comparative Test |
| | | 50 μM | 100 μM | 200 μM | |
|---|---|---|---|---|---|
| 0 | 98% | 68% | 80% | 82% | 16% |
| 1 | 2% | 7% | 6% | 6% | 41% |
| 2 | 0% | 6% | 4% | 6% | 12% |
| 3 | 0% | 7% | 3% | 2% | 9% |
| 4 | 0% | 6% | 3% | 2% | 9% |
| 5 | 0% | 6% | 4% | 2% | 13% |

Table 2 indicates that when the test liquid containing Compound (1) was sprayed onto rice, the onset of *Burkholderia glumae* was prevented even when the culture solution for infection containing *Burkholderia glumae* was also sprayed onto the same rice. In contrast, the comparative test wherein the culture solution for infection containing *Burkholderia glumae* was sprayed onto rice after spraying water, the onset of *Burkholderia glumae* infection was observed in many of the rice samples.

Test Example 6

A test liquid and a culture solution for infection were prepared in the same manner as in Test Example 5, and the culture solution for infection was sprayed onto Korean rice (Milyang 23) raised in a hothouse until the flowering stage. One hour after the spraying, each test liquid (10 mL) was sprayed onto the rice. After cultivation for seven days, the onset of *Burkholderia glumae* infection on the rice was evaluated in the same manner as in Test Example 4. The same evaluation was conducted as the comparative test in the same manner except that water was used instead of the test liquid. Further, the same evaluation was conducted to serve as a blank using water instead of both the test liquid and the culture solution for infection.

Table 3 shows the results.

TABLE 3

| Score | Blank | Compound (1) | | | Comparative Test |
| | | 50 μM | 100 μM | 200 μM | |
|---|---|---|---|---|---|
| 0 | 98% | 88% | 85% | 89% | 23% |
| 1 | 2% | 2% | 5% | 3% | 48% |
| 2 | 0% | 4% | 3% | 3% | 8% |
| 3 | 0% | 2% | 3% | 2% | 4% |
| 4 | 0% | 2% | 2% | 2% | 5% |
| 5 | 0% | 2% | 2% | 1% | 12% |

Table 3 indicates that, similar to Test Example 4, when the test liquid containing Compound (1) was sprayed onto the rice, the onset of *Burkholderia glumae* was prevented even when the culture solution for infection containing *Burkholderia glumae* was also sprayed onto the same rice. In contrast, in the comparative test wherein the culture solution for infection containing *Burkholderia glumae* was sprayed onto rice after spraying water, the onset of *Burkholderia glumae* infection was observed in many rice samples.

Test Example 7

Using the flow cell system shown in FIG. 4, the *Burkholderia aeruginosa* biofilm formation inhibition effect of Compound (2), which was produced using Production Example 2, was evaluated.

Flow Cell System

A culture medium bottle (1), peristaltic pump (2), glass cell (4) and waste fluid bottle (5) are connected via a silicon tube (6) so that a culture medium (9) is supplied to the glass cell (4) from the culture medium bottle (1) using the peristaltic pump (2). The system includes an air removal section (3) between the peristaltic pump (2) and a turncock (7a) for removing entrained air. All components in the flow cell system were sterilized using gamma rays or an autoclave.

As described later, the inhibitory effect against biofilm formation of each of the compounds can be examined in the following manner. Bacteria are cultured in a glass cell (4) to grow a biofilm on the inner wall of the cell, and a test liquid containing one of the compounds is applied to the biofilm. Then the state of the biofilm is observed to evaluate the inhibitory effect against biofilm formation of the compound using a spectral confocal and multiphoton microscope (Leica TCS SP2: produced by Leica).

Materials

Bacteria:

The bacteria were prepared by inserting a pTdk-LVAgfp plasmid into a *Burkholderia aeruginosa* PAO1-strain using the electroportion method so that the *Burkholderia aeruginosa* PAO1-strain is transformed to express Green Fluorescent Protein (hereinafter referred to as "gfp expression PAO1-strain") (see Teresa R. et al., Applied and Environmental Microbiology, April 2001, pp. 1865-1873).

Culture Medium:

A 30-mM glucose-containing FAB culture medium was used for culture solution, and a 0.3-mM glucose-containing FAB culture medium was used for main cultivation.

The glucose-containing FAB culture medium was prepared by adding 200 μg/mL of carbenicillin to an aqueous solution containing 30 mM glucose or 0.3 mM glucose, 15 mM ammonium sulfate, 33.7 mM disodium hydrogenphosphate dihydrate, 22.1 mM potassium dihydrogen phosphate, 51.7 mM sodium chloride, 0.47 mM magnesium chloride, 0.08 mM calcium chloride and the following 0.1% trace metal solution.

Trace Metal Solution: An aqueous solution containing 1.16 mM calcium sulfate dihydrate, 0.72 mM iron sulfate heptahydrate, 0.08 mM manganous sulfate monohydrate, 0.08 mM copper sulfate pentahydrate, 0.07 mM zinc sulfate heptahydrate, 0.04 mM cobalt sulfate heptahydrate, 0.04 mM sodium permanganate monohydrate, and 0.08 mM boric acid.

Bacterial Suspension: A gfp expression PAO1-strain was inoculated into a 30 mM glucose-containing FAB culture medium, and was subjected to shake culturing at 37° C. in an isothermal tank overnight. The obtained overnight culture liquid was diluted by a 30 mM glucose-containing FAB culture medium to $OD_{590}=0.1$.

Test Liquid and Control Test Liquid:

Test liquid: The test liquid was prepared by dissolving Compound (2) produced in Example 2 in such a manner that 100 μM of DMSO solution of Compound (2) was obtained. The resulting DMSO solution was added to a 0.3 mM glucose-containing FAB culture medium so that the concentration of the compound became 0.1% (v/v).

Control Test Liquid: A control test liquid was prepared in the same manner as the test liquid except that DMSO not containing the compound was used.

Test Method

The flow cell system was filled with ethanol of 70 volume %, and was allowed to stand for at least 12 hours to sterilize the system. Then, air that had been filtered by a membrane filter (8a) was supplied into the flow cell system using a peristaltic pump (2) to dry the system. Thereafter, the system was filled with a 0.3 mM glucose-containing FAB culture medium. 500 µL of a broth was injected into a glass cell (4) from the upper surface using a syringe, and the glass cell was sealed by turning off three-way turncocks (7a,7b). The cell as such was allowed to stand for 1 hour at room temperature.

After static culturing, the two three-way turncocks (7a,7b) were turned on, so as to supply the test liquid and control test liquid each at a flow rate of 200 µL per minute. With a spectral confocal and multiphoton microscope, the process of biofilm formation (deposition) by the *Burkholderia aeruginosa* (gfp expression PAO1-strain) that adhered to the inner wall of the glass cell was observed three-dimensionally from above to observe changes over time (after 1 hour, 48 hours, 60 hours, 72 hours, and 84 hours). Note that the test liquid and the control test liquid were replaced with fresh liquids every 36 hours.

Figure 5:
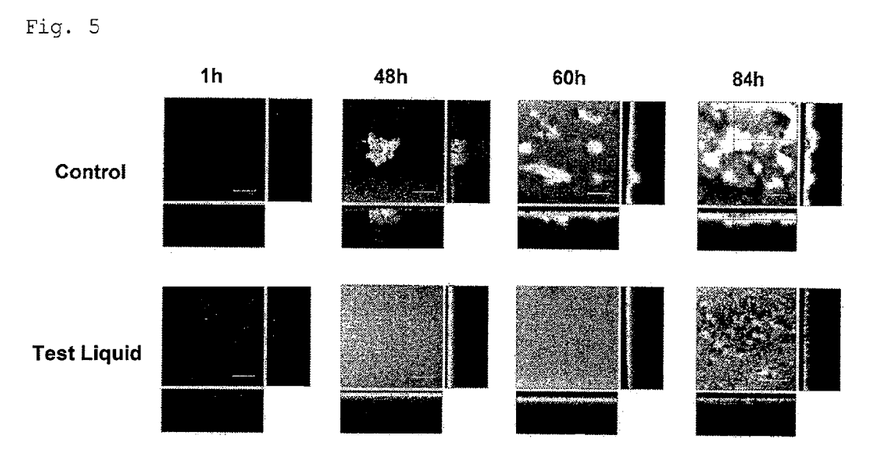
FIG. 5 shows the results of Test Example 7 wherein the states of biofilm formation are compared when using a test liquid and when using a control test liquid (control).

FIG. 5 shows comparison results between the biofilm conditions when the test liquid was used and those when the control test liquid was used (control test). FIG. 5 shows three-dimensional conditions of *Burkholderia aeruginosa* (gfp expression PAO1-strain) that adhered to the inner wall of the glass cell in the respective experiments, with front views of the inner wall of the glass cell and cross-sectional (vertical and horizontal) views of the glass cell.

As is clear from those results, in the control test using the control test liquid, it was observed that *Burkholderia* aeruginosa (gfp expression PAO1-strain) formed a huge, thick biofilm; however, in the test using the test liquid such biofilm formation was not observed. This indicates that Compound (2) can inhibit biofilm formation or remove an already formed biofilm.

Test Example 8

Using the flow cell system shown in FIG. 4, the *Porphyromonas gingivalis* biofilm formation inhibition effect of Compound (2), which was produced in Production Example 2, was evaluated.
Materials
Bacteria: Periodontitis pathogenic bacteria *Porphyromonas gingivalis* 381-strain (clinical strain) were used.
Culture Medium: A GAM culture medium containing 5 µg/L hemin and 1 µg/L menadione was used.
Bacterial Suspension The 381-strain was inoculated into the GAM culture medium, and cultivated until the stationary phase ($OD_{550}$=1.8). Then the culture medium was diluted 20-fold by the GAM culture medium described above.
Test Liquid and Control Test Liquid:
Test liquid: The test liquid was prepared by dissolving Compound (2) into DMSO to obtain 100 µM of DMSO solution of Compound (2). The resulting DMSO solution was added to the culture medium so that the concentration of the compound became 0.1% (v/v).
Control Test Liquid:
A control test liquid was prepared in the same manner as the test liquid except that DMSO not containing the compound was used.
Test Method The glass cell (4) of the flow cell system was replaced with a stainless cell (3×7×120 mm), and 10 hydroxyapatite (HA) disks (6 mm in diameter, 1 mm in thickness) were placed in the cell. The HA disks had been subjected to salivary treatment overnight.

The test liquid and control test liquid were each circulated in the system at a flow rate of 8 mL/min for 14 days. The test liquid and control test liquid were replaced with fresh liquids every two days.

After the cultivation, the HA disks were dipped in 300 µL of sterile distilled water, and treated by supersonic waves for 30 minutes at 4° C. The biofilms formed on the HA disks were peeled off and suspended in distilled water. Then, the turbidity of 10 µL of the suspension liquid was measured with an absorptiometer (C07500 calorimeter, produced by Funakoshi) (measurement wavelength=550 nm).

A mean OD was found based on the resulting OD values, excluding the minimum and maximum values. Likewise, the turbidity of the control test liquid was obtained and determined as a control OD value, and then the control mean OD value was found in the same manner. A biofilm formation inhibition rate (Inhibition Rate) was obtained by the following formula.

Biofilm formation inhibition rate(%)=100−{(mean OD value)/(control mean OD value)}×100

Table 4 shows the results.

TABLE 4

| Concentration of Compound (µM) | Mean OD Value | Control Mean OD value | Inhibition Rate (%) |
|---|---|---|---|
| 100 | 0.041 | 0.094 | 56.4 |

Test Example 9

*Burkholderia glumae* was inoculated into an LB culture medium (produced by BD (Difco LB Broth: containing tryptone (10.0 g), yeast extract (5.0 g), and sodium chloride (10.0 g)), and cultured at 37° C. overnight. The thus-obtained culture solution was subjected to bacterial collection using a centrifuge, and washed with an LB culture medium twice using a fresh LB culture medium each time. To the bacterial cell a fresh LB culture medium was added, and then Compound (1) produced in Production Example 1 was added thereto in such a manner that its final concentration became a predetermined value (i.e., 0, 20, 40, 60, 80 or 100 µM), followed by shake culturing for 20 hours. The amount of toxoflavin produced by the bacterial cell in the culture solution was obtained by the following procedure.

Each culture solution was filtered by a 0.22-µm membrane filter, and 1 mL of the filtrate was isolated. One mL of chloroform was added to the filtrate, followed by extraction. The thus-obtained chloroform layer was concentrated under reduced pressure, and an 80% (V/V) an aqueous methanol solution was added to and dissolved in the residue. The absorbance (at 260 nm) of the solution was measured, and the toxin doses were calculated from the calibration curve, which was obtained using chemically synthesized standard toxin.

Figure 6:
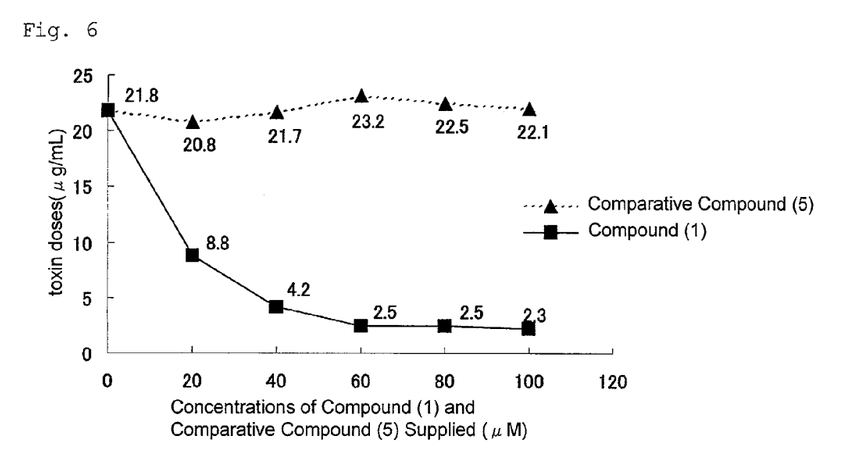
FIG. 6 is a graph showing the relationship between the concentrations (μM) of Compound (1) and Comparative Compound (5) supplied in Test Example 9 and the toxin doses (μg/mL).

The same test was conducted as in the comparative test using the compound shown below (Comparative Compound (5)), which is disclosed in Patent Document 3. FIG. 6 shows the results.

Comparative Compound (5)

As is clear from FIG. 6, when Compound (1) of the present invention produced in Production Example 1 was added to *Burkholderia glumae*, the toxin doses produced by bacteria remarkably decreased as the concentration of Compound (1) increased. In contrast, when Comparative Compound (5) was added to *Burkholderia glumae*, the toxin doses produced by bacteria exhibited almost no change even when the concentration of Comparative Compound (5) was increased.

The invention claimed is:

1. A biofilm formation inhibitor and/or biofilm remover of *Burkholderia aeruginosa* and/or periodontopathic bacteria comprising:

a pyrimidinone compound represented by General Formula (1):

(1)

wherein $R^1$ is a $C_{1-5}$ alkyl group or a phenyl group; and $R^2$ is a hydrogen atom or a $C_{1-5}$ alkyl group; provided that when $R^2$ is a hydrogen atom, $R^1$ cannot be a methyl group; and an additive selected from the group consisting of antibiotics, antimicrobial agents, bactericides, antiseptic agents, builders, bleaching agents, and enzymes.

2. The biofilm formation inhibitor and/or biofilm remover of *Burkholderia aeruginosa* and/or periodontopathic bacteria according to claim 1, wherein $R^1$ is a $C_{2-5}$ alkyl group, and $R^2$ is a hydrogen atom.

3. The biofilm formation inhibitor and/or biofilm remover of *Burkholderia aeruginosa* and/or periodontopathic bacteria according to claim 1, wherein $R^1$ is a $C_{1-3}$ alkyl group, and $R^2$ is a $C_{1-5}$ alkyl group.

4. A bacterial disease control agent for agricultural and horticultural use comprising:

a pyrimidinone compound represented by General Formula (1):

(1)

wherein $R^1$ is a $C_{1-5}$ alkyl group or a phenyl group; and $R^2$ is a hydrogen atom or a $C_{1-5}$ alkyl group; provided that when $R^2$ is a hydrogen atom, $R^1$ cannot be a methyl group; and an additive selected from the group consisting of herbicides, insecticides, nematicides, miticides, bactericides, plant growth regulators, synergists, and soil conditioners.

5. The bacterial disease control agent for agricultural and horticultural use according to claim 4, wherein $R^1$ is a $C_{2-5}$ alkyl group, and $R^2$ is a hydrogen atom.

6. The bacterial disease control agent for agricultural and horticultural use according to claim 4, wherein $R^1$ is a $C_{1-3}$ alkyl group, and $R^2$ is a $C_{1-5}$ alkyl group.

7. The bacterial disease control agent for agricultural and horticultural use according to claim 6, wherein $R^2$ is a methyl group.

8. An agricultural and horticultural bacterial disease-control method, comprising the step of:

applying to cultivated plants a pyrimidinone compound represented by General Formula (1):

(1)

wherein $R^1$ is a $C_{1-5}$ alkyl group or a phenyl group; and $R^2$ is a hydrogen atom or a $C_{1-5}$ alkyl group; provided that when $R^2$ is a hydrogen atom, $R^1$ cannot be a methyl group.

9. A method of preventing the formation of a biofilm formed by *Burkholderia aeruginosa* and/or periodontopathic bacteria or a method of removing a biofilm formed by *Burkholderia aeruginosa* and/or periodontopathic bacterial wherein the method comprises employing a pyrimidinone compound represented by General Formula (1):

(1)

wherein $R^1$ is a $C_{1-5}$ alkyl group or a phenyl group; and $R^2$ is a hydrogen atom or a $C_{1-5}$ alkyl group; provided that when $R^2$ is a hydrogen atom, $R^1$ cannot be a methyl group.